(12) United States Patent
Tsaur

(10) Patent No.: US 7,056,049 B2
(45) Date of Patent: Jun. 6, 2006

(54) SHOCK RESISTANT APPLICATOR FOR NON-EVAPORATIVE LIQUID

(76) Inventor: Garry Tsaur, 19222 Tranbarger St., Rowland Heights, CA (US) 91748

( * ) Notice: Subject to any disclaimer, the term of this patent is extended or adjusted under 35 U.S.C. 154(b) by 0 days.

(21) Appl. No.: 10/654,799

(22) Filed: Sep. 4, 2003

(65) Prior Publication Data

US 2005/0053413 A1    Mar. 10, 2005

(51) Int. Cl.
*B43K 5/14*   (2006.01)
*B43K 5/02*   (2006.01)
*B65D 25/08*  (2006.01)

(52) U.S. Cl. .................. 401/133; 401/40; 206/219
(58) Field of Classification Search ............ 401/40–43, 401/132–135; 206/219–222
See application file for complete search history.

(56) References Cited

U.S. PATENT DOCUMENTS

| | | | | | |
|---|---|---|---|---|---|
| 1,109,033 | A | * | 9/1914 | Bixby | 401/40 |
| 1,524,635 | A | * | 1/1925 | Siegel | 401/40 |
| 2,025,110 | A | * | 12/1935 | Kingman | 401/40 |

* cited by examiner

*Primary Examiner*—David J. Walczak
(74) *Attorney, Agent, or Firm*—Joe Nieh

(57) ABSTRACT

A shock resistant applicator for non-evaporative liquid comprises an elongated tubular housing sealed on one end enclosing a first liquid near the sealed end separated from a second liquid by a viscous substance. The elongated tubular housing has an opening mechanism near the sealed end to release the enclosed liquids through the open end of the elongated tubular housing. A shock resistant plug is disposed near the open end of the elongated tubular housing and defines a small through hole from the liquid to the open end of the elongated tubular housing. The shock resistant plug will prevent the none-evaporative second liquid from being unintentionally released from the elongated tubular housing by dramatically increasing the surface tension of the second liquid near the open end of the elongated tubular housing.

17 Claims, 3 Drawing Sheets

SHOCK RESISTANT APPLICATOR FOR NON-EVAPORATIVE LIQUID

BACKGROUND

1. Field of Invention

The present invention relates generally to an applicator for liquids. More specifically the present invention relates to a hollow tube swab applicator that contains the liquids for application.

2. Description of Related Art

Swab applicator generally comprises of a tubular handle with a formed absorbent tip at one or both of the two ends of the tubular handle. The absorbent tip may be made of cotton or a foam absorbent material. The tip may also be a brush. The tubular handle may be made of wood, paper, or plastic and it may be solid or hollow.

Swab applicators have a variety of applications. Swab applicators are a convenient and sanitary means for applying and removing a variety of substances such as liquids, lotions, creams, and various chemicals and medications.

SUMMARY OF THE INVENTION

The present invention is a shock resistant applicator for non-evaporative liquid. The shock resistant applicator for non-evaporative liquid comprises an elongated tubular housing sealed on one end enclosing a first liquid near the sealed end separated from a second liquid by a viscous substance. The elongated tubular housing has an opening means near the sealed end to release the enclosed liquids through the open end of the elongated tubular housing. A shock resistant plug is disposed near the open end of the elongated tubular housing and defines a small through hole from the liquid to the open end of the elongated tubular housing. The shock resistant plug will prevent the none-evaporative second liquid from being unintentionally released from the elongated tubular housing when it is subjected to shock due to rough handling or dropping of the applicator by dramatically increasing the surface tension of the second liquid near the open end of the elongated tubular housing. If the second liquid is an evaporative liquid, another viscous substance may be placed between the second liquid and the shock resistant plug to prevent evaporation of the second liquid.

DETAILED DESCRIPTION OF THE PREFERRED EMBODIMENT

Figure 1:
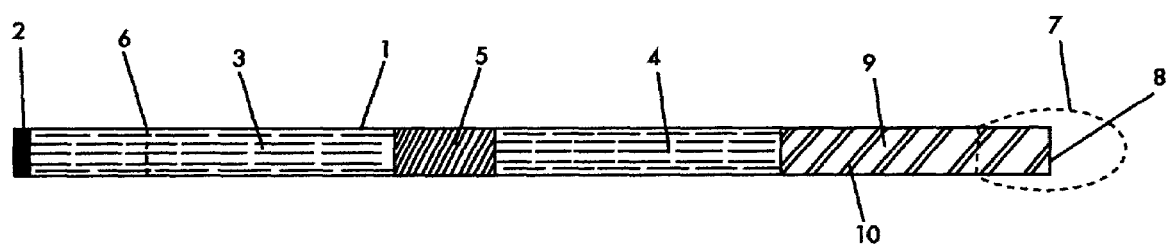
FIG. 1 shows the preferred embodiment of the shock resistant applicator for non-evaporative liquid.
Figure 1A:
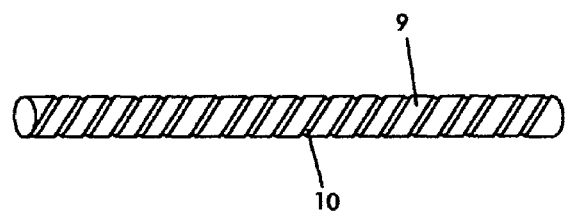
FIG. 1A shows the enlarged view of the shock resistant plug.
Figure 2:
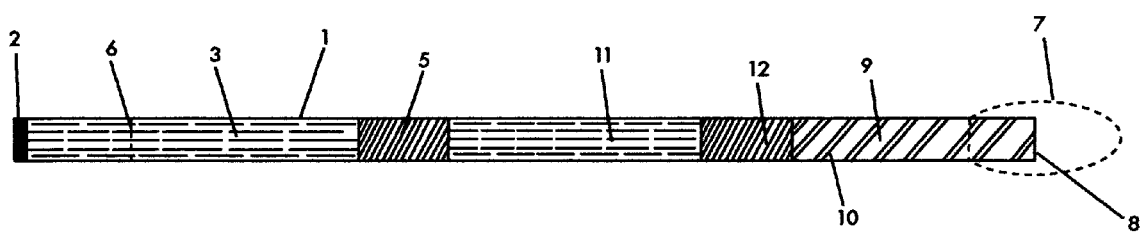
FIG. 2 shows another embodiment of the shock resistant applicator for non-evaporative liquid.

FIG. 1 shows the preferred embodiment of the present invention. In the preferred embodiment the shock resistant applicator for non-evaporative liquid comprises a swab applicator comprising an elongated tubular housing 1 sealed on one end 2 enclosing a first liquid 3 near the sealed end 2 separated from a second liquid 4 by a viscous substance 5. The elongated tubular housing 1 has an opening means 6 near the sealed end 2 to release the enclosed liquids 3, 4 to an applicator tip 7 affixed to the other open end 8 of the elongated tubular housing 1. The viscous substance 5 may be silicone or any other substance capable of separating the two liquids 3, 4 yet allow the first liquid 3 to flow through it when the opening means 6 is opened to allow atmospheric pressure to enter near the sealed end 2 of the elongated tubular housing 1. The opening means 6 may be a simple score line, a reduced cross section, or any other suitable opening means that will allow air to enter near the sealed end 2 of the elongated tubular housing 1 when it is opened. A shock resistant plug 9 is disposed near the open end 8 of the elongated tubular housing 1 and defines a small through hole 10 from the liquids 3, 4 to the applicator tip 7. The through hole 10 may be a straight through hole or a spiraling through hole near the inside diameter of the elongated tubular housing 1 as shown in FIG. 1A. The length of the shock resistant plug 9 and the diameter of the through hole 10 may be selected to control the flow rate of the liquids 3, 4 out of the elongated tubular housing 1. When the liquids 3, 4 are released into the applicator tip 7 by allowing air to enter the elongated tubular housing 1 through the opening means 6, the liquids 3, 4 in the moisturized applicator tip 7 may be applied to desired surfaces. The applicator tip 7 may be made of any absorbent material such as cotton or sponge or may be in the form of a brush. The shock resistant plug 9 will prevent the none-evaporative second liquid 4 from being unintentionally released from the elongated tubular housing 1 when it is subjected to shock due to rough handling or dropping of the applicator by dramatically increasing the surface tension of the second liquid 4 near the open end 8 of the elongated tubular housing 1. If the second liquid 11 is an evaporative liquid, another viscous substance 12 may be placed between the second liquid 11 and the shock resistant plug 9 as shown in FIG. 2 to prevent evaporation of the second liquid 11. The small through hole 10 defined by the shock resistant plug 9 may also be sealed with a wax plug that may be forced open by bending and compressing the elongated tubular housing 1. An optional cap may be attached to the open end 8 of the elongated housing 1.

Figure 3:
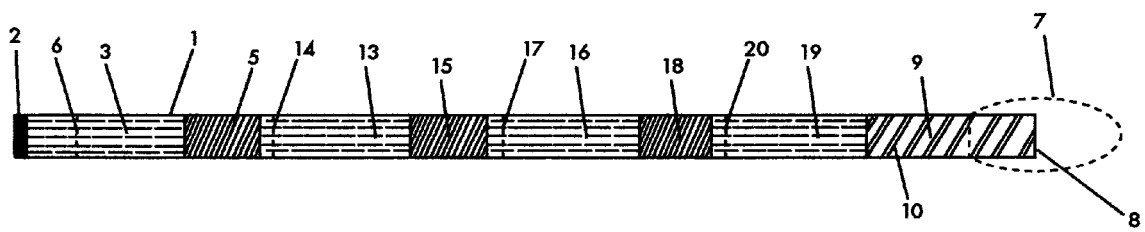
FIG. 3 shows another embodiment of the shock resistant applicator for non-evaporative liquid.

FIG. 3 shows another embodiment of the shock resistant applicator for non-evaporative liquid wherein multiple liquids 3, 13, 16, 19 and viscous substances 5, 15, 18 may be disposed in alternating positions within the elongated tubular housing 1 with opening means 6, 14, 17, 20 positioned at the location of each liquid section located near the end furthest from the opened end 8. In this embodiment, various combinations of the liquids may be selectively released into the applicator tip 7 or different amount of the same liquid may be selectively released into the applicator tip 7.

Figure 4:
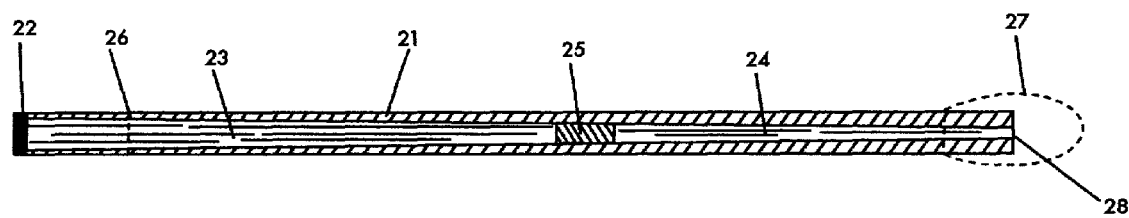
FIG. 4 shows another embodiment of the shock resistant applicator for non-evaporative liquid.

FIG. 4 shows another embodiment of the shock resistant applicator for non-evaporative liquid wherein the internal diameter of the elongated tubular housing 21 narrows from the sealed end 22 to a greatly reduced internal diameter at the open end 28. The elongated tubular housing 21 is sealed on one end 22 enclosing a first liquid 23 near the sealed end 22 separated from a second liquid 24 by a viscous substance 25. The elongated tubular housing 21 has an opening means 26 near the sealed end 22 to release the enclosed liquids 23, 24 to an applicator tip 27 affixed to the other open end 28 of the elongated tubular housing 21. The viscous substance 25 may be silicone or any other substance capable of separating the two liquids 23, 24 yet allow the first liquid 23 to flow through it when the opening means 26 is opened to allow atmospheric pressure to enter near the sealed end 22 of the elongated tubular housing 21. The opening means 26 may be a simple score line, a reduced cross section, or any other suitable opening means that will allow air to enter near the sealed end 22 of the elongated tubular housing 21 when it is opened. In this embodiment, a separate shock resistant plug is not necessary. The greatly reduced internal diameter of the elongated tubular housing 21 itself acts as the shock resistant plug to prevent the none-evaporative second liquid 24 from being unintentionally released from the elongated tubular housing 21 when it is subjected to shock due to rough handling or dropping of the applicator by dramatically increasing the surface tension of the second liquid 24 near the open end 28 of the elongated tubular housing 21. The open end 28 may also be sealed with a wax plug that may be forced open by bending and compressing the elongated tubular housing 21.

Figure 5:
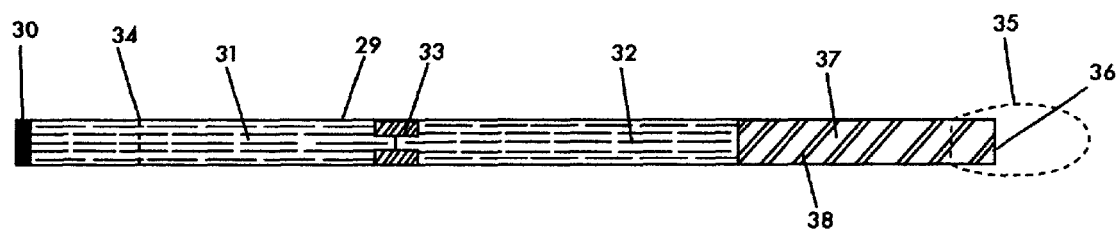
FIG. 5 shows another embodiment of the shock resistant applicator for non-evaporative liquid.

FIG. 5 shows another embodiment of the shock resistant applicator for non-evaporative liquid wherein the two liquids 31, 32 in the elongated tubular housing 29 are not separated by a viscous substance between them but rather a reduced section 33 in the inside diameter of the elongated tubular housing 29 positioned at the interface between the liquids 31, 32 will maintain the separation of the two liquids 31, 32. The opening at the reduced section is predetermined such that the surface tension at the interface of the two liquids 31, 32 themselves will be capable of maintaining the separation of the two liquids 31, 32, particularly when the first liquids 31 is water based and the second liquid 32 is oil based. A viscous substance similar to the one shown in FIG. 2 may also be disposed within the elongated tubular housing 29 between the second liquid 32 from the shock resistant plug 37 to further separate the second liciuid 32 from the shock resistant plug 37.

Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A shock resistant applicator for non-evaporative liquid comprising:
    an elongated tubular housing sealed on one end enclosing a predetermined quantity of a first liquid near the sealed end separated from a second liquid by a viscous substance with an opening means near the sealed end to release the enclosed liquids through the other open end of the elongated tubular housing; and
    a shock resistant plug disposed near the open end of the elongated tubular housing defining a small through hole from the liquid to the open end of the elongated tubular housing;
    wherein the liquids may be released out of the elongated tubular housing by allowing air to enter the elongated tubular housing through the opening means.

2. A shock resistant applicator for non-evaporative liquid as in claim 1, wherein said small through hole defined by the shock resistant plug is sealed with a wax plug that may be forced open by bending and compressing the elongated tubular housing.

3. A shock resistant applicator for non-evaporative liquid as in claim 1, wherein the small through hole defined by the shock resistant plug is in a non-linear path from the liquid to the open end of the elongated tubular housing.

4. A shock resistant applicator for non-evaporative liquid as in claim 1, wherein the small through hole from the liquid to the open end of the elongated tubular housing defined by the shock resistant plug is a spiraling path formed by the interface between a spiraling channel on the exterior surface of the shock resistant plug and the interior surface of the elongated tubular housing.

5. A shock resistant applicator for non-evaporative liquid as in claim 1, wherein a second viscous substance is disposed within the elongated tubular housing separating the second liquid from the shock resistant plug.

6. A shock resistant applicator for non-evaporative liquid comprising:
    an elongated tubular housing sealed on one end enclosing multiple liquids and multiple viscous substances disposed in alternating positions within the elongated tubular housing with multiple opening means positioned at predetermined locations to release the enclosed liquids through the other open end of the elongated tubular housing; and
    a shock resistant plug disposed near the open end of the elongated tubular housing defining a small through hole from the liquid to the open end of the elongated tubular housing;
    wherein the liquids may be released out of the elongated tubular housing by allowing air to enter the elongated tubular housing through the opening means.

7. A shock resistant applicator for non-evaporative liquid as in claim 6, wherein said small through hole defined by the shock resistant plug is sealed with a wax plug that may be forced open by bending and compressing the elongated tubular housing.

8. A shock resistant applicator for non-evaporative liquid as in claim 6, wherein the small through hole defined by the shock resistant plug is in a non-linear path from the liquid to the open end of the elongated tubular housing.

9. A shock resistant applicator for non-evaporative liquid as in claim 6, wherein the small through hole from the liquid to the open end of the elongated tubular housing defined by the shock resistant plug is a spiraling path formed by the interface between a spiraling channel on the exterior surface of the shock resistant plug and the interior surface of the elongated tubular housing.

10. A shock resistant applicator for non-evaporative liquid as in claim 6, wherein a second viscous substance is disposed within the elongated tubular housing separating the second liquid from the shock resistant plug.

11. A shock resistant applicator for non-evaporative liquid comprising an elongated tubular housing sealed on one end with inside diameters that taper from the sealed end to the other open end and enclosing a first liquid separated from a second liquid by a viscous substance between them with an opening means near the sealed end to release the enclosed liquids through the other open end of the elongated tubular housing wherein the liquids may be released out of the elongated tubular housing by allowing air to enter the elongated tubular housing through the opening means.

12. A shock resistant applicator for non-evaporative liquid as in claim 11, wherein said open end is sealed with a wax plug that may be forced open by bending and compressing the elongated tubular housing.

13. A shock resistant applicator for non-evaporative liquid comprising:
    an elongated tubular housing sealed on one end enclosing a predetermined quantity of a first liquid near the sealed end and a second liquid wherein said elongated tubular housing has a smaller diameter, which is not obstructed by any valve, near the interface between the first liquid and the second liquid with an opening means near the sealed end to release the enclosed liquids through the other open end of the elongated tubular housing; and a shock resistant plug disposed near the open end of the elongated tubular housing and defining a small through hole from the liquid to the open end of the elongated tubular housing;

wherein the liquids may be released out of the elongated tubular housing by allowing air to enter the elongated tubular housing through the opening means.

14. A shock resistant applicator for non-evaporative liquid as in claim 13, wherein said small, through hole defined by the shock resistant plug is sealed with a wax plug that may be forced open by bending and compressing the elongated tubular housing.

15. A shock resistant applicator for non-evaporative liquid as in claim 13, wherein the small through hole defined by the shock resistant plug is in a non-linear path from the liquid to the open end of the elongated tubular housing.

16. A shock resistant applicator for non-evaporative liquid as in claim 13, wherein the small through hole from the liquid to the open end of the elongated tubular housing defined by the shock resistant plug is a spiraling path formed by the interface between a spiraling channel on the exterior surface of the shock resistant plug and the interior surface of the elongated tubular housing.

17. A shock resistant applicator for non-evaporative liquid as in claim 13, wherein a viscous substance is disposed within the elongated tubular housing separating the second liquid from the shock resistant plug.

* * * * *